(12) United States Patent
Terada

(10) Patent No.: US 8,530,398 B2
(45) Date of Patent: Sep. 10, 2013

(54) AQUEOUS HAIR CLEANSING AGENT

(75) Inventor: Eiji Terada, Tokyo (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 13/805,193

(22) PCT Filed: Jun. 13, 2011

(86) PCT No.: PCT/JP2011/003343
§ 371 (c)(1),
(2), (4) Date: Dec. 18, 2012

(87) PCT Pub. No.: WO2011/158483
PCT Pub. Date: Dec. 22, 2011

(65) Prior Publication Data
US 2013/0102513 A1    Apr. 25, 2013

(30) Foreign Application Priority Data
Jun. 18, 2010    (JP) ................ 2010-139514

(51) Int. Cl.
*A61K 8/73* (2006.01)
(52) U.S. Cl.
USPC ........... 510/123; 510/127; 510/130; 424/70.1
(58) Field of Classification Search
None
See application file for complete search history.

(56) References Cited

U.S. PATENT DOCUMENTS

| | | | |
|---|---|---|---|
| 6,221,816 B1 | 4/2001 | Kasuga et al. | |
| 7,947,258 B2 * | 5/2011 | Terada | 424/70.122 |
| 2007/0269397 A1 | 11/2007 | Terada | |
| 2009/0124523 A1 | 5/2009 | Dol et al. | |
| 2009/0253603 A1 | 10/2009 | Uchiyama et al. | |
| 2010/0222246 A1 | 9/2010 | Doi et al. | |
| 2012/0015894 A1 | 1/2012 | Terada | |
| 2012/0022037 A1 | 1/2012 | Terada | |

FOREIGN PATENT DOCUMENTS

| | | |
|---|---|---|
| JP | 11-080797 | 3/1999 |
| JP | 2001-107096 A | 4/2001 |
| JP | 2001-213762 A | 8/2001 |
| JP | 2006-265547 A | 10/2006 |
| JP | 2007-197420 A | 8/2007 |
| JP | 2007-211232 A | 8/2007 |
| JP | 2008-31468 A | 2/2008 |
| JP | 2008-69084 A | 3/2008 |
| JP | 2009-263331 | 11/2009 |
| WO | WO 2007/116586 A1 | 10/2007 |

OTHER PUBLICATIONS

International Search Report issued Jul. 26, 2011 in PCT/JP2011/003343 filed Jun. 13, 2011.
International Preliminary Report on Patentability and Written Opinion issued Jan. 24, 2013 in PCT/JP2011/003343 filed Jun. 13, 2011.
Japanese Office Action issued May 7, 2013 in Application No. 2010-139514 filed Jun. 18, 2010.

* cited by examiner

*Primary Examiner* — Necholus Ogden, Jr.
(74) *Attorney, Agent, or Firm* — Oblon, Spivak, McClelland, Maier & Neustadt, L.L.P.

(57) ABSTRACT

The aqueous hair cleansing agent of the present invention contains components (A), (B), (C), and (D) below:
(A) a sulfate type anionic surfactant represented by the general formula (1) below $$R^1O(CH_2CH_2O)_nSO_3M \quad (1);$$

(B) a polyoxypropylene alkyl ether type nonionic surfactant represented by the general formula (2) below $$R^2O(CH_2CH(CH_3)O)_mH \quad (2);$$

(C) a monoalkyl glyceryl ether or monoalkenyl glyceryl ether type nonionic surfactant having an alkyl group or alkenyl group having 4 to 12 carbon atoms; and
(D) an alkylhydroxysulfobetaine type amphoteric surfactant represented by the general formula (3) below

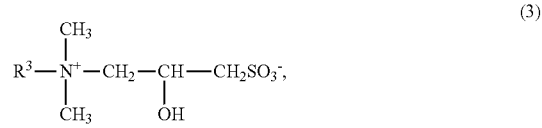

the mass ratio of components (B) and (D) being (B)/(D) =3/2 to 1/4.

20 Claims, No Drawings

AQUEOUS HAIR CLEANSING AGENT

FIELD OF THE INVENTION

The present invention relates to an aqueous hair cleansing agent.

BACKGROUND OF THE INVENTION

In the case of a conventional aqueous hair cleansing agent, if the scalp is soiled due to sebum, or a styling agent is attached to the hair, lather and foam quality, which are basic aspects of performance are degraded, and it is difficult for sufficient cleansing power to be exhibited.

In order to obtain an aqueous hair cleansing agent having good lather and high cleansing power, it is preferable to use, as a main cleansing agent, a strong acid-based anionic surfactant having the same charge as that of the hair and the scalp. In order to further enhance lather and cleansing power, an auxiliary surfactant such as a nonionic surfactant or an amphoteric surfactant is generally formulated therewith. Among the auxiliary surfactants, the ones that are most commonly used in aqueous hair cleansing agents are a fatty acid monoethanolamide as the nonionic surfactant and a fatty acid amidopropyl betaine as the amphoteric surfactant, but when the amount of sebum is large or when a styling agent is used, lather is poor and it is difficult for sufficient cleansing power to be exhibited.

Therefore, in order to enhance the lather of a cleansing agent,

Patent Documents 1 to 3 disclose a technique of using a strong acid-type anionic surfactant in combination with a monoalkyl glyceryl ether or a polyoxypropylene octyl ether as a nonionic surfactant.

RELATED DOCUMENTS

Patent Documents

[Patent Document 1] Japanese patent publication No. JP-A-2001-107096
[Patent Document 2] Japanese patent publication No. JP-A-2007-197420
[Patent Document 3] Japanese patent publication No. JP-A-2008-031468

SUMMARY OF THE INVENTION

In accordance with the present invention, there is provided an aqueous hair cleansing agent containing components (A), (B), (C), and (D) below:

(A) from 1 to 30 weight % of a sulfate type anionic surfactant represented by the general formula (1) below $$R^1O(CH_2CH_2O)_nSO_3M \tag{1}$$

wherein in the general formula (1) above, $R^1$ presents an alkyl group or alkenyl group having 10 to 18 carbon atoms, M presents an alkali metal, an alkaline earth metal, ammonium, an alkanolamine, or a basic amino acid, and n presents a number from 0 to 5 as a mass average;

(B) from 0.1 to 10 weight % of a polyoxypropylene alkyl ether type nonionic surfactant represented by the general formula (2) below, $$R^2O(CH_2CH(CH_3)O)_mH \tag{2}$$

wherein in the general formula (2) above, $R^2$ presents a straight chain or branched alkyl group or alkenyl group having 8 to 10 carbon atoms, and m presents a number from 0.5 to 4 as a mass average;

(C) from 0.1 to 5 weight % of a monoalkyl glyceryl ether or monoalkenyl glyceryl ether type nonionic surfactant having an alkyl group or alkenyl group having 4 to 12 carbon atoms; and (D) from 0.1 to 10 weight % of an alkylhydroxysulfobetaine type amphoteric surfactant represented by the general formula (3) below

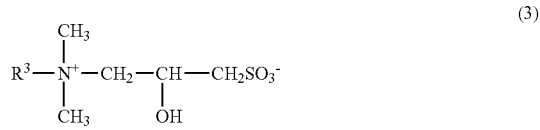

wherein in the general formula (3) above, $R^3$ presents an alkyl group having 10 to 14 carbon atoms, the mass ratio of components (B) and (D) being (B)/(D) =3/2 to 1/4.

DESCRIPTION OF THE INVENTION

Even if the cleansing agents described in Patent Documents 1 to 3 are used, the lather and cleansing power are not sufficient when there is a large amount of sebum or styling agent.

The present invention relates to an aqueous hair cleansing agent exhibiting sufficient lather and high cleansing power even under conditions in which there is sebum or a styling agent.

The present inventor has found that an aqueous hair cleansing agent having excellent lather and cleansing power even under conditions of a large amount of sebum and the like is obtained for the first time by mixing, with an aqueous hair cleansing agent having an alkyl sulfate or an alkyl ether sulfate, which are sulfate type anionic surfactants, as a main cleansing component, a polyoxypropylene alkyl ether, a monoalkyl glyceryl ether or a monoalkenyl glyceryl ether, and an alkylhydroxysulfobetaine at a specific ratio as auxiliary surfactants.

In accordance with the present invention, there is obtained an aqueous hair cleansing agent having excellent lather and cleansing power even under conditions in which there is soiling due to sebum and the like.

The aqueous hair cleansing agent of the present invention is an aqueous hair cleansing agent containing components (A), (B), (C), and (D) below:

(A) from 1 to 30 weight % of a sulfate type anionic surfactant represented by the general formula (1) below $$R^1O(CH_2CH_2O)_nSO_3M \tag{1}$$

wherein in the general formula (1) above, $R^1$ presents an alkyl group or alkenyl group having 10 to 18 carbon atoms, M presents an alkali metal, an alkaline earth metal, ammonium, an alkanolamine, or a basic amino acid, and n presents a number from 0 to 5 as a mass average (B) from 0.1 to 10 weight % of a polyoxypropylene alkyl ether type nonionic surfactant represented by the general formula (2) below $$R^2O(CH_2CH(CH_3)O)_mH \tag{2}$$

wherein in the general formula (2) above, $R^2$ presents a straight chain or branched alkyl group or alkenyl group having 8 to 10 carbon atoms, and m presents a number from 0.5 to 4 as a mass average (C) from 0.1 to 5 weight % of a monoalkyl glyceryl ether or monoalkenyl glyceryl ether type nonionic surfactant having an alkyl group or alkenyl group having 4 to 12 carbon atoms (D) from 0.1 to 10 weight % of an alkylhydroxysulfobetaine type amphoteric surfactant represented by the general formula (3) below

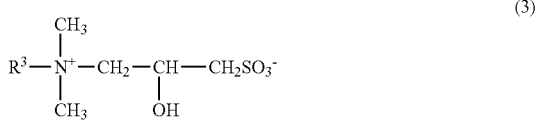

wherein in the general formula (3) above, R³ presents an alkyl group having 10 to 14 carbon atoms, the mass ratio of components (B) and (D) being (B)/(D)=3/2 to 1/4.

First, component (A) is explained.

In the aqueous hair cleansing agent of the present invention, component (A) is an alkyl sulfate or an alkyl ether sulfate, which are sulfate type anionic surfactants, represented by the general formula (1).

$$R^1O(CH_2CH_2O)_nSO_3M \quad (1)$$

In the general formula (1) above, R¹ presents an alkyl group or alkenyl group having 10 to 18 carbon atoms, M presents an alkali metal, an alkaline earth metal, ammonium, an alkanolamine, or a basic amino acid, and n presents a number from 0 to 5 as a mass average.

Among them, a polyoxyethylene alkyl ether sulfate for which R¹ in the general formula (1) above is an alkyl group having 12 to 14 carbon atoms, n presents 1 or 2 as a mass average, and M is ammonium or sodium is more preferable from the viewpoint of lather (quantity) and high cleansing power.

With regard to component (A), one type thereof may be used or two or more types may be used in combination, and the content thereof is 1 to 30 weight % of the aqueous hair cleansing agent of the present invention, preferably 5 to 25 weight %, more preferably 8 to 20 weight %, and even more preferably 9 to 15 weight %, in terms of lather (quantity) and viscosity of the aqueous hair cleansing agent.

Component (B) is now explained.

In the aqueous hair cleansing agent of the present invention, component (B) is a polyoxypropylene alkyl ether type nonionic surfactant represented by the general formula (2).

$$R^2O(CH_2CH(CH_3)O)_mH \quad (2)$$

In the general formula (2) above, R² presents a straight chain or branched alkyl group or alkenyl group having 8 to 10 carbon atoms, and m presents a number from 0.5 to 4 as a mass average.

Among them, a polyoxypropylene octyl ether for which R² in the general formula (2) above is an alkyl group having 8 carbon atoms and m is a number from 2 to 3 as a mass average is more preferable from the viewpoint of quick lathering, smoothness during rinsing and after drying, and suppression of strange odor as a starting material.

With regard to component (B), one type thereof may be used or two or more types may be used in combination, and the content thereof is 0.1 to 10 weight % of the aqueous hair cleansing agent of the present invention, preferably 0.2 to 5 weight %, more preferably 0.3 to 2 weight %, and even more preferably 0.5 to 1.5 weight %, in terms of lather (quantity) and smoothness during rinsing.

Component (C) is now explained.

In the aqueous hair cleansing agent of the present invention, component (C) is a monoalkyl glyceryl ether or monoalkenyl glyceryl ether type nonionic surfactant having an alkyl group or alkenyl group having 4 to 12 carbon atoms.

Among them, the alkyl group or alkenyl group is preferably a straight chain or branched alkyl group having 4 to 10 carbon atoms, and more preferably a straight chain or branched alkyl group having 8 to 10 carbon atoms, from the viewpoint of quick lathering and cleansing power. Specific examples include an n-butyl group, an isobutyl group, an n-pentyl group, a 2-methylbutyl group, an isopentyl group, an n-hexyl group, an isohexyl group, an n-heptyl group, an n-octyl group, a 2-ethylhexyl group, an n-decyl group, and an isodecyl group. Among them, a branched alkyl group is preferable, and a 2-ethylhexyl group and an isodecyl group are more preferable.

With regard to component (C), one type thereof may be used or two or more types may be used in combination, and the content thereof is 0.1 to 5 weight % of the aqueous hair cleansing agent of the present invention, preferably 0.2 to 3 weight %, and more preferably 0.3 to 1.5 weight %, in terms of lather and cleansing power.

Component (D) is now explained.

In the aqueous hair cleansing agent of the present invention, component (D) is an alkylhydroxysulfobetaine type amphoteric surfactant represented by the general formula (3) below.

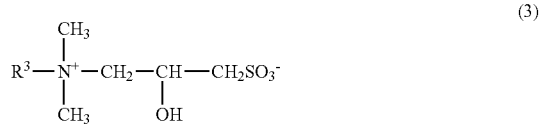

In the general formula (3) above, R³ presents an alkyl group having 10 to 14 carbon atoms.

Among them, R³ in the general formula (3) above is more preferably an alkyl group having 12 to 14 carbon atoms from the viewpoint of lather and cleansing power under conditions in which there is soiling due to sebum and the like, and the viscosity of the aqueous hair cleansing agent.

With regard to component (D), one type thereof may be used or two or more types may be used in combination, and the content thereof is 0.1 to 10 weight % of the aqueous hair cleansing agent of the present invention, preferably 0.3 to 5 weight %, and more preferably 0.5 to 3 weight %, in terms of lather and cleansing power under conditions in which there is soiling due to sebum and the like, and the viscosity of the aqueous hair cleansing agent.

On the other hand, with regard to the alkylhydroxysulfobetaine as component (D), which is an amphoteric surfactant used in the present invention, since the anionic group is a strong acid-based sulfonic acid group, even if the pH is 4 or below, since the anionic group is dissociated, it has the properties of an amphoteric surfactant without being influenced by pH and it can exhibit high lather and cleansing power even under conditions in which there is soiling due to sebum, regardless of the pH.

Furthermore, the mass ratio of components (B) and (C) is preferably (B)/(C)=3/1 to 1/2, and more preferably 2/1 to 1/1, from the viewpoint of lather and cleansing power under conditions in which there is soiling due to sebum and the like, smoothness during foaming and during rinsing, and smoothness, softness, and manageability after drying.

Furthermore, the mass ratio of component (B) and (D) is preferably (B)/(D)=3/2 to 1/4, and more preferably 3/2 to 1/3, from the viewpoint of lather and cleansing power under conditions in which there is soiling due to sebum and the like, smoothness during foaming and during rinsing, and smoothness, softness, and manageability after drying.

The aqueous hair cleansing agent of the present invention can provide higher lather and cleansing power by containing a combination of components (A) to (D) above at a specific ratio and can provide hair that is smooth during foaming and during rinsing by reducing friction of the hair and hair that is smooth, soft, and easy to manage after drying.

The aqueous hair cleansing agent of the present invention may have further formulated therewith (E) an organic carboxylic acid or a salt thereof in order to improve smoothness and manageability after drying.

The organic carboxylic acid is preferably a dicarboxylic acid (optionally having a hydroxy group) or a hydroxymonocarboxylic acid. Specifically, examples of the dicarboxylic acid optionally having a hydroxy group include malonic acid, succinic acid, glutaric acid, adipic acid, maleic acid, fumaric acid, phthalic acid, oxalic acid, malic acid, and tartaric acid, and examples of the hydroxymonocarboxylic acid include glycolic acid, lactic acid, hydroxyacrylic acid, oxybutyric acid, and glyceric acid. Among them, glycolic acid, lactic acid, malonic acid, maleic acid, and malic acid are preferable. Lactic acid and malic acid are more preferable. Furthermore, examples of a salt of these organic carboxylic acids include a salt with an alkali metal, an alkaline earth metal, ammonia, or an organic amine compound.

With regard to the organic carboxylic acid or a salt thereof, one type thereof may be used or two or more types may be used in combination, and the content thereof is preferably 0.1 to 5 weight % of the aqueous hair cleansing agent, more preferably 0.2 to 3 weight %, and even more preferably 0.5 to 2 weight %, in terms of it being higher than the quantity that is used for the purpose of simply adjusting the pH and providing hair smoothness and manageability after drying.

The aqueous hair cleansing agent of the present invention when diluted 20 times with water preferably has a pH at 25° C. of 1 to 5, more preferably a pH of 2 to 4.5, and even more preferably a pH of 3 to 4, in terms of the organic carboxylic acid making the hair exhibit the maximum smoothness and manageability.

In order to further improve the cleansing performance, the aqueous hair cleansing agent of the present invention may contain an anionic surfactant other than component (A), a nonionic surfactant other than components (B) and (C), or an amphoteric surfactant other than component (D).

As the anionic surfactant other than component (A), a sulfuric acid-based, sulfonic acid-based, or carboxylic acid-based surfactant may be used. Examples thereof include an alkylene sulfosuccinate phenyl alkyl ether sulfate, a sulfosuccinate alkyl ester salt, a polyoxyalkylene sulfosuccinate alkyl ester salt, an alkanesulfonate, a higher fatty acid salt, and an alkyl ether carboxylic acid and a salt thereof; among them an alkyl ether carboxylic acid or a salt thereof is preferable, and an alkyl ether carboxylic acid or a salt thereof having an alkyl group having 12 to 14 carbon atoms is more preferable, from the viewpoint of low irritation and smoothness during rinsing.

Examples of the nonionic surfactant other than components (B) and (C) include a polyoxyalkylene sorbitan fatty acid ester, a polyoxyalkylene sorbitol fatty acid ester, a polyoxyalkylene glycerol fatty acid ester, a polyoxyalkylene fatty acid ester, a polyoxyalkylene alkyl ether, a polyoxyalkylene alkyl phenyl ether, a polyoxyalkylene (hardened) castor oil, a sucrose fatty acid ester, a polyglycerol alkyl ether, a polyglycerol fatty acid ester, a fatty acid alkanolamide, and an alkylglycoside.

Among them, a polyoxyalkylene sorbitan fatty acid ester such as a polyoxyethylene sorbitan fatty acid ester, a polyoxyalkylene fatty acid ester such as a polyoxyalkylene ($C_8$ to $C_{20}$) fatty acid ester, a polyoxyethylene alkyl ether such as a polyoxyethylene lauryl ether, a polyoxyalkylene (hardened) castor oil such as polyoxyethylene hardened castor oil, and an alkylglycoside are preferable from the viewpoint of lather (foam quantity). A polyoxyethylene alkyl ether having an alkyl group having 12 to 18 carbon atoms is more preferable.

Furthermore, a fatty acid alkanolamide is also suitable; either a monoalkanolamide or a dialkanolamide may be used, and one having an acyl group having 8 to 18 carbon atoms and, even more, 10 to 16 carbon atoms is preferable from the viewpoint of lather (foam quantity). Furthermore, one having a hydroxyalkyl group having 2 to 3 carbon atoms is preferable, and examples thereof include oleic acid diethanolamide, palm kernel oil fatty acid diethanolamide, coconut oil fatty acid diethanolamide, lauric acid diethanolamide, polyoxyethylene coconut oil fatty acid monoethanolamide, coconut oil fatty acid monoethanolamide, lauric acid isopropanolamide, and lauric acid monoethanolamide.

Examples of the amphoteric surfactant other than component (D) include betaine-based surfactants. Among them, an alkyldimethylaminoacetic acid betaine or a fatty acid amidopropyl betaine is preferable from the viewpoint of lather (foam quantity) and viscosity, and a fatty acid amidopropyl betaine is more preferable. The fatty acid amidopropyl betaine is preferably one having an acyl group having 8 to 18 carbon atoms, and more preferably 10 to 16 carbon atoms, and is even more preferably lauramidopropyl betaine, palm kernel oil fatty acid amidopropyl betaine, coconut oil fatty acid amidopropyl betaine, and the like. When an amphoteric surfactant other than component (D) is formulated therewith, the content thereof is preferably no greater than the content of component (D), more preferably no greater than 0.5 weight %, and even more preferably no greater than 1/3 as a ratio by mass relative to component (D).

With regard to the surfactants other than (A), (B), (C), and (D), one type or two or more types may be used in combination in the aqueous hair cleansing agent, but when the aqueous hair cleansing agent of the present invention is prepared in the form of an aqueous liquid cleansing agent, it is more preferable to use, together with components (A), (B), (C), and (D), a fatty acid amidopropyl betaine and a fatty acid alkanolamide since appropriate viscosity and a smooth feel during rinsing are obtained.

The content of the surfactants other than (A), (B), (C), and (D) is preferably 0.01 to 10 weight % of the aqueous hair cleansing agent of the present invention since a good foam-increasing effect is obtained. It is more preferably 0.1 to 8 weight %, even more preferably 0.2 to 4 weight %, and even more preferably 0.5 to 1.5 weight % from the above-mentioned point.

In order to improve ease of running the fingers through the hair during rinsing and finishing after drying, a cationic surfactant, a cationized polymer, and a silicone may be formulated with the aqueous hair cleansing agent of the present invention.

(Cationic Surfactant)

Examples of the cationic surfactant include an alkyltrimethylammonium salt, an alkoxytrimethylammonium salt, a dialkyldimethylammonium salt, an alkyldimethylamine salt, an alkoxydimethylamine salt, and an alkylamidodimethylamine salt.

(i) Alkyltrimethylammonium Salt

Examples include those represented by the general formula below.

$$R^{11}-N^+(Me)_3X^- \qquad (4)$$

In the general formula (4) above, $R^{11}$ presents an alkyl group having 12 to 22 carbon atoms, Me presents a methyl group, and X presents a halogen (chlorine or bromine).

Specific examples include cetyltrimethylammonium chloride, stearyltrimethylammonium chloride and behenyltrimethylammonium chloride.
(ii) Alkoxytrimethylammonium Salt
Examples include those represented by the general formula below.

$$R^{12}-O-R^{13}-N^+(Me)_3 X^- \quad (5)$$

In the general formula (5) above, $R^{12}$ presents an alkyl group having 12 to 22 carbon atoms, $R^{13}$ presents an ethylene group or a propylene group, Me presents a methyl group, and X presents a halogen (chlorine or bromine).

Specific examples include stearoxypropyltrimethylammonium chloride, stearoxyethyltrimethylammonium chloride, and stearoxyhydroxypropyltrimethylammonium chloride.
(iii) Dialkyldimethylammonium Salt
Examples include those represented by the general formula below.

$$R^{14}{}_2-N^+(Me)_2 X^- \quad (6)$$

In the general formula (6) above, $R^{14}$ presents an alkyl group having 12 to 22 carbon atoms or a benzyl group, Me presents a methyl group, and X presents a halogen (chlorine or bromine).

Specific examples include distearyldimethylammonium chloride.
(iv) Alkyldimethylamine Salt
Examples include those represented by the general formula below.

$$R^{15}-N(Me)_2 \quad (7)$$

In the general formula (7), $R^{15}$ presents an alkyl group having 12 to 22 carbon atoms, and Me presents a methyl group.

Specific examples include an organic acid salt of behenyldimethylamine and stearyldimethylamine.
(v) Alkoxydimethylamine Salt
Examples include those represented by the general formula below.

$$R^{16}-O-R^{17}-N(Me)_2 \quad (8)$$

In the general formula (8), $R^{16}$ presents an alkyl group having 12 to 22 carbon atoms, $R^{17}$ presents an ethylene group or a propylene group, and Me presents a methyl group.
(vi) Alkylamidodimethylamine Salt
Examples include those represented by the general formula below.

$$R^{18}-C(=O)NH^{19}-N(Me)_2 \quad (9)$$

In the general formula (9) above, $R^{18}$ presents an alkyl group having 11 to 21 carbon atoms, $R^{19}$ presents an ethylene group or a propylene group, and Me presents a methyl group.

Examples of the cationic surfactant other than (i) to (vi) above include lanolin fatty acid aminopropylethyldimethylammonium ethylsulfate (ethylsulfate of an alkanoylaminopropyldimethylethylammonium, the alkanoyl group being derived from lanolin), lanolin fatty acid aminoethyltriethylammonium ethylsulfate, lanolin fatty acid aminopropyltriethylammonium ethylsulfate, lanolin fatty acid aminoethyltrimethylammonium methylsulfate, lanolin fatty acid aminopropylethyldimethylammonium methylsulfate, isoalkanoic acid ($C_{14}$ to $C_{20}$) aminopropylethyldimethylammonium ethylsulfate, isoalkanoic acid ($C_{18}$ to $C_{22}$) aminopropylethyldimethylammonium ethylsulfate, isostearic acid aminopropylethyldimethylammonium ethylsulfate, isononanoic acid aminopropylethyldimethylammonium ethylsulfate, and an alkyltrimethylammonium saccharide.

With regard to the cationic surfactant, two or more types thereof may be used in combination, and the content thereof is preferably 0.01 to 10 weight % of the aqueous hair cleansing agent of the present invention, more preferably 0.05 to 5 weight %, and even more preferably 0.1 to 2 weight %, in terms of smoothness from the time of washing hair to the time of rinsing.
(Cationized Polymer)

Next, as the cationized polymer, there can be cited a cationized cellulose derivative, a cationic starch, a cationized fenugreek gum derivative, a cationized guar gum derivative, a cationized tara gum derivative, a cationized locust bean gum derivative, a cationized quassia derivative, a cationized xanthan gum derivative, a diallyl quaternary ammonium salt/acrylamide copolymer, a vinylimidazolium trichloride/vinylpyrrolidone copolymer, a hydroxyethylcellulose/dimethyldiallylammonium chloride copolymer, a vinylpyrrolidone/quaternized dimethylaminoethyl methacrylate copolymer, a polyvinylpyrrolidone/alkylamino acrylate copolymer, a polyvinylpyrrolidone/alkylamino acrylate/vinylcaprolactam copolymer, a vinylpyrrolidone/methacrylamidopropyltrimethylammonium chloride copolymer, an alkylacrylamide/acrylate/alkylaminoalkylacrylamide/polyethylene glycol methacrylate copolymer, an adipic acid/dimethylamino hydroxypropylethylenetriamine copolymer (Cartaretin, Sandoz, USA), cationic polymers described in JP-A-53-139734 and JP-A-60-36407, and the like; among them, a cationized cellulose derivative, a cationized fenugreek gum derivative, a cationized guar gum derivative, a cationized tara gum derivative, a cationized locust bean gum derivative, and a diallyl quaternary ammonium salt/acrylamide copolymer are preferable. A cationized cellulose derivative and a cationized guar gum derivative are more preferable.

Furthermore, for example, commercially available products such as Merquat 550 (NALCO, copolymer of acrylamide and a diallyldimethylammonium salt; CTFA name Polyquaternium-7), Luviquat FC370 (BASF, copolymer of 1-vinyl-2-pyrrolidone and 1-vinyl-3-methylimidazolium salt; CTFA name Polyquaternium-16), Gafquat 755N (ISP, copolymer of 1-vinyl-2-pyrrolidone and dimethylaminoethyl methacrylate; CTFA name Polyquaternium-11), Ucare Polymer JR and the Ucare LR series (Amerchol, salt of reaction product between trimethylammonium substituted epoxide and hydroxyethylcellulose; CTFA name Polyquaternium-10), Poiz C-60H, Poiz C-80M, and Poiz C-150L (Kao Corporation, salt of reaction product between trimethylammonium substituted epoxide and hydroxyethylcellulose; CTFA name Polyquaternium-10), the Jaguar series (Rhodia, salt of reaction product between trimethylammonium substituted epoxide and guar gum), Catinal CF-100 (Toho Chemical Industry Co., Ltd., salt of reaction product between trimethylammonium substituted epoxide and fenugreek gum), Catinal CTR-100 (Toho Chemical Industry Co., Ltd., salt of reaction product between trimethylammonium substituted epoxide and tara gum), and Catinal CLB-100 (Toho Chemical Industry Co., Ltd., salt of reaction product between trimethylammonium substituted epoxide and locust bean gum) may be used.

With regard to these cationized polymers, two or more types may be used in combination, and the content thereof is preferably 0.01 to 3 weight % of the aqueous hair cleansing agent of the present invention, more preferably 0.05 to 2 weight %, and even more preferably 0.1 to 1 weight %, in terms of smoothness from the time of washing hair to the time of rinsing.

(Silicones)
Examples of silicones include those listed below.
(i) Polydimethylsiloxane
Examples include those represented by the general formula below.

$$(Me)_3Si-[(Me)_2SiO]_d-(Me)_3 \qquad (10)$$

In the general formula (10) above, Me presents a methyl group and d is a number from 3 to $2\times10^4$.

A polydimethylsiloxane is present as dispersed particles in the aqueous hair cleansing agent, and the average particle size of the dispersed particles is preferably 0.1 to 100 μm, more preferably 0.1 to no greater than 30 μm, even more preferably 0.1 to no greater than 4 μm, and even more preferably 0.1 to no greater than 2 μm, from the viewpoint of finishing after drying and storage stability of the aqueous hair cleansing agent.

The average particle size of a polydimethylsiloxane emulsion is the median diameter measured by a laser light scattering method, and it may be measured using a normal particle size analyzer employing laser light scattering, for example an LS-130 from Coulter.

As a polydimethylsiloxane, for example, ones commercially available as 'Silicone CF2450' by Dow Corning Toray Silicone Co., Ltd. containing 60 weight % of a polydimethylsiloxane oil for which d in the general formula (10) is 300 to 6,500 and having an average particle size of 0.8 μm, or 'Silicone CF2460' by Dow Corning Toray Silicone Co., Ltd. containing 75 weight % of a polydimethylsiloxane oil for which d is 300 to 6,500 and having an average particle size of 20 μm may be used.

Such a polydimethylsiloxane is preferably contained at 0.01 to 10 weight % of the aqueous hair cleansing agent of the present invention, more preferably 0.05 to 6 weight %, even more preferably 0.3 to 3 weight %, and even more preferably 0.5 to 2 weight %, in terms of improving foam texture during hair washing, and texture and luster after drying.

(ii) Amino-Modified Silicone

Various types of amino-modified silicones may be used, and those having an average molecular weight of about $3\times10^3$ to $1\times10^5$ and described under the name Amodimethicone in the CTFA Dictionary (Cosmetic Ingredient Dictionary, USA) $9^{th}$ Edition, 2002, Volume 1, p. 107 are more preferable. Examples of commercially available products include SM 8704C (Dow Corning Toray Silicone Co., Ltd.), DC 929 (Dow Corning Corporation), KT 1989 (GE Toshiba Silicone Co., Ltd.), 8500 Conditioning Agent, DOW CORNING TORAY SS-3588, and DOW CORNING TORAY SILSTYLE 104 (Dow Corning Toray Silicone Co., Ltd.).

(iii) Other Silicones

Other than those mentioned above, there can be cited a polyether-modified silicone, a polymethylphenylsiloxane, a fatty acid-modified silicone, an alcohol-modified silicone, an alkoxy-modified silicone, an epoxy-modified silicone, a fluorine-modified silicone, a cyclic silicone, an alkyl-modified silicone, and the like.

With regard to these amino-modified silicones and the other silicones, two or more types may be used in combination, and the content thereof is preferably 0.01 to 5 weight % of the aqueous hair cleansing agent of the present invention, more preferably 0.05 to 2 weight %, and even more preferably 0.1 to 1 weight %, in terms of smoothness from the time of washing the hair to the time of rinsing.

The aqueous hair cleansing agent of the present invention may further contain a pearlescent agent containing an ethylene glycol monofatty acid ester, an ethylene glycol difatty acid ester, an ethylene glycol monoalkyl ether, or an ethylene glycol dialkyl ether.

Examples of the ethylene glycol monofatty acid ester include ethylene glycol monostearic acid ester and ethylene glycol monobehenic acid ester, and examples of the ethylene glycol difatty acid ester include ethylene glycol distearic acid ester and ethylene glycol dibehenic acid ester. Examples of the ethylene glycol monoalkyl ether include ethylene glycol monostearyl ether, and examples of the ethylene glycol dialkyl ether include ethylene glycol distearyl ether.

Among them, ethylene glycol distearic acid ester is preferable from the viewpoint of a pearl appearance.

With regard to the above, two or more types may be used in combination, and the content thereof is preferably 0.1 to 10 weight % of the aqueous hair cleansing agent of the present invention, more preferably 0.5 to 5 weight %, and even more preferably 1 to 4 weight %, in terms of improving the storage stability of the aqueous hair cleansing agent, improving smoothness during foaming and during rinsing, and improving the stability of the aqueous hair cleansing agent.

Furthermore, the aqueous hair cleansing agent of the present invention may comprise an oil as another conditioning agent. Examples of the oil include hydrocarbons such as squalene, squalane, liquid paraffin, liquid isoparaffin, and cycloparaffin; glycerides such as castor oil, cacao oil, mink oil, avocado oil, olive oil, sunflower oil, and camellia oil; waxes such as beeswax, spermaceti, lanolin, and carnauba wax; alcohols such as cetyl alcohol, oleyl alcohol, stearyl alcohol, isostearyl alcohol, 2-octyldodecanol, glycerol, myristyl alcohol, behenyl alcohol, and cetostearyl alcohol; esters such as isopropyl palmitate, isopropyl myristate, octyldodecyl myristate, hexyl laurate, cetyl lactate, propylene glycol monostearate, oleyl oleate, hexadecyl 2-ethylhexanoate, isononyl isononanoate, and tridecyl isononanoate; higher fatty acids such as capric acid, lauric acid, myristic acid, palmitic acid, stearic acid, behenic acid, oleic acid, coconut oil fatty acid, isostearic acid, and isopalmitic acid; and in addition isostearyl glyceryl ether, polyoxypropylene butyl ether, and the like. Among them, a higher fatty acid, a higher alcohol, and a glyceride are preferable, and lauric acid, myristyl alcohol, cetyl alcohol, stearyl alcohol, sunflower oil, and camellia oil are more preferable. With regard to these oils, one type thereof may be used or two or more types may be used in combination, and the content thereof is preferably 0.1 to 2 weight % of the aqueous hair cleansing agent of the present invention, more preferably 0.2 to 1.5 weight %, and even more preferably 0.3 to 1.0 weight %.

The aqueous hair cleansing agent of the present invention may comprise a viscosity adjusting agent; examples of the viscosity adjusting agent include hydroxyethylcellulose, methylcellulose, polyethylene glycol, polypropylene glycol, ethylene glycol, propylene glycol, isoprene glycol, ethanol, benzyl alcohol, benzyloxyethanol, phenoxyethanol, a clay mineral, and a salt (sodium chloride, ammonium chloride, sodium citrate, and the like), and among them benzyl alcohol, ethanol, polypropylene glycol, sodium chloride, and sodium citrate are preferable. With regard to the viscosity adjusting agent, two or more types may be used in combination, and the amount thereof used is preferably 0.01 to 5 weight % of the aqueous hair cleansing agent of the present invention, more preferably 0.05 to 4 weight %, and even more preferably 0.1 to 3 weight %, in terms of foam quantity and foam quality.

The aqueous hair cleansing agent of the present invention may contain, in addition to the above-mentioned components, a component that is usually used in an aqueous hair cleansing agent as appropriate according to the intended purpose. Examples of such a component include a preservative; a chelating agent; a moisturizing agent such as sorbitol or panthenol; a coloring agent such as a dye or a pigment; an extract such as a polar solvent extract of eucalyptus, a protein obtained from a pearl or a mother-of-pearl-containing shell or a hydrolysate thereof, a protein obtained from honey, royal jelly, or silk or a hydrolysate thereof, an extract containing a protein obtained from legume seeds, a ginseng extract, a rice germ extract, a fucus extract, an aloe extract, an *Alpinia speciosa* leaf extract, or a chlorella extract; a pearlescent agent such as titanium oxide; a fragrance; a pigment; a UV absorber; an antioxidant; and other components described in Encyclopedia of Shampoo Ingredients (Hunting, Anthony L. L., 1983, MICELLE PRESS).

The form of the aqueous hair cleansing agent of the present invention may be selected as appropriate from a liquid, a gel, and the like, but is preferably a liquid using as a solvent water or a lower alcohol, and more preferably water.

The present invention is not limited to the above-mentioned embodiments, and modification, improvement, and the like within the scope that can achieve the present invention are included in the present invention.

EXAMPLES

Examples and Comparative Examples

The aqueous hair cleansing agents shown in Table 1 were prepared by a standard method and evaluated by the evaluation methods below. The results are shown in Tables 1 and 2. The pH is a value at 25° C. when diluted 20 times by mass with water.

(1) Foam Quantity

A bundle of human hair having a length of 25 cm, a width of 5.5 cm, and a weight of 20 g was preliminarily washed using 2 g of a 10 weight % aqueous solution of sodium lauryl ether (2) sulfate, fully rinsed with hot water at 40° C., and then, in a state in which it contained 30 g of moisture, coated with 0.1 g of model sebum (mixed liquid of S-lanolin 50 weight %, L-lanolin 45 weight %, oleic acid 5%) and 2 g of the aqueous hair cleansing agent, followed by foaming for 15 seconds. Subsequently, the foam was squeezed out from the hair into a volumetric flask, and the volume of the foam was measured. The larger the value, the better the lather under conditions of sebum soiling.

(2) Cleansing Power

The cleansing power was determined by measuring change in color before and after cleansing using a colorimeter when model sebum colored with carbon black was used.

First, a circle having a diameter of 3 cm was drawn on an upper arm part, and the color inside the circle was measured using a colorimeter. When measuring using a colorimeter, the L value, a value, and b value were measured, and the initial values were defined as $L_0$, $a_0$, and $b_0$ respectively. Subsequently, model sebum (S-lanolin 50 weight %, L-lanolin 45 weight %, oleic acid 5%, carbon black 0.1 weight %) colored with carbon black was spread uniformly inside the circle drawn on the upper arm part, and measurement with the colorimeter was carried out again ($L_1$, $a_1$, $b_1$). Subsequently, the upper arm part was coated with 0.1 g of an aqueous solution of the aqueous hair cleansing agent diluted to 10 weight %, massaged for 30 seconds, then rinsed with hot water at 40 degrees for 30 seconds, and measured using the colorimeter ($L_2$, $a_2$, $b_2$) after wiping off the moisture.

The cleansing power (%) was calculated from the equation below using the values obtained by measurement using the colorimeter.

$$\text{Cleansing power (\%)} = \left(1 - \frac{\sqrt{(L_2-L_0)^2+(a_2-a_0)^2+(b_2-b_0)^2}}{\sqrt{(L_1-L_0)^2+(a_1-a_0)^2+(b_1-b_0)^2}}\right) \times 100$$

(3) Slippery Feel During Foaming

A bundle of human hair having a length of 25 cm, a width of 5.5 cm, and a weight of 10 g was lightly rinsed with hot water at 40° C., excess moisture was removed, and foaming was carried out using 0.5 g of the aqueous hair cleansing agent for about 30 seconds. In this process, sensory evaluation of a slippery feel was carried out using the 5 grades below. Evaluation was carried out by five people, and the average value was obtained. An average of at least 4.0 was denoted as 'excellent', at least 3.2 but less than 4.0 as 'good', at least 2.5 but less than 3.2 as 'fair', and less than 2.5 as 'poor'.
5: very slippery
4: fairly slippery
3: normal feel
2: not very slippery
1: not slippery (4) Slippery Feel During Rinsing A bundle of human hair having a length of 25 cm, a width of 5.5 cm, and a weight of 10 g was lightly rinsed with hot water at 40° C., excess moisture was removed, and foaming was carried out using 0.5 g of the aqueous hair cleansing agent for about 30 seconds. Subsequently, while rinsing the hair bundle having foam attached thereto with hot water at 40° C. and a flow rate of 2 L/min, sensory evaluation of a slippery feel was carried out using the 5 grades below. Evaluation was carried out by five people, and the average value was obtained. An average of at least 4.0 was denoted as 'excellent', at least 3.2 but less than 4.0 as 'good', at least 2.5 but less than 3.2 as 'fair', and less than 2.5 as 'poor'.
5: very slippery
4: fairly slippery
3: normal feel
2: not very slippery
1: not slippery (5) Slippery Feel after Drying After being treated under the same conditions as for (4), the hair was dried using a drier, and sensory evaluation of a slippery feel after being fully dried was carried out using the 5 grades below. Evaluation was carried out by five people, and the average value was obtained. An average of at least 4.0 was denoted as 'excellent', at least 3.2 but less than 4.0 as 'good', at least 2.5 but less than 3.2 as 'fair', and less than 2.5 as 'poor'.
5: very slippery
4: fairly slippery
3: normal feel
2: not very slippery
1: not slippery (6) Softness after Drying After being treated under the same conditions as for (4), sensory evaluation of the softness of hair after drying was carried out using the 5 grades below. Evaluation was carried out by five people, and the average value was obtained. An average of at least 4.0 was denoted as 'excellent', at least 3.2 but less than 4.0 as 'good', at least 2.5 but less than 3.2 as 'fair', and less than 2.5 as 'poor'.
5: soft
4: slightly soft
3: normal feel
2: not very soft
1: not soft (7) Manageability after Drying After being treated under the same conditions as for (4), sensory evaluation of the manageability after drying was carried out using the 5 grades below. Evaluation was carried out by five people, and the average value was obtained. An average of at least 4.0 was denoted as 'excellent', at least 3.2 but less than 4.0 as 'good', at least 2.5 but less than 3.2 as 'fair', and less than 2.5 as 'poor'.

5: manageable
4: slightly manageable
3: normal feel
2: not very manageable
1: not manageable

TABLE 1

| | Component (weight %) | Example 1 | 2 | 3 | 4 | 5 | 6 | 7 | 8 |
|---|---|---|---|---|---|---|---|---|---|
| (A) | Ammonium lauryl ether (1) sulfate[*1] | 12 | 12 | 12 | 12 | 11 | 11 | 9.5 | 13 |
| | Sodium lauryl ether (2) sulfate[*2] | — | — | — | — | — | — | — | — |
| (B) | Polyoxypropylene (3) octyl ether | 1 | 0.5 | 1 | 1.5 | 1 | 1.5 | 1 | 2.2 |
| | Polyoxypropylene (2) octyl ether | — | — | — | — | — | — | — | — |
| (B') | Polyoxypropylene (5) octyl ether | — | — | — | — | — | — | — | — |
| | Polyoxyethylene (3) octyl ether | — | — | — | — | — | — | — | — |
| (C) | Isodecyl glyceryl ether | 0.5 | 1 | 1 | 0.5 | 1 | 0.5 | 0.5 | 0.8 |
| | 2-Ethylhexyl glyceryl ether | — | — | — | — | — | — | — | — |
| (C') | Coconut oil fatty acid monoethanolamide | — | — | — | — | — | — | — | — |
| (D) | Laurylhydroxysulfobetaine | 1.5 | 1.5 | 1 | 1 | 2 | 2 | 3 | 1.5 |
| (D') | Amidopropyl betaine laurate | — | — | — | — | — | — | — | — |
| Others | Malic acid | 0.75 | 0.75 | 0.75 | 0.75 | 0.75 | 0.75 | 0.75 | 0.75 |
| | Ethylene glycol distearyl ether | 2 | 2 | 2 | 2 | 2 | 2 | 2 | 2 |
| | Cationized Guar gum[*3] | 0.5 | 0.5 | 0.5 | 0.5 | 0.5 | 0.5 | 0.5 | 0.5 |
| | Dimethylpolysiloxane emulsion[*4] | 1 | 1 | 1 | 1 | 1 | 1 | 1 | 1 |
| | Benzyl alcohol | 0.3 | 0.3 | 0.3 | 0.3 | 0.3 | 0.3 | 0.3 | 0.3 |
| | Polypropylene (7) glycol | 1 | 1 | 1 | 1 | 1 | 1 | 1 | 1 |
| | Sodium chloride | 0.3 | 0.3 | 0.3 | 0.3 | 0.3 | 0.3 | 0.3 | 0.3 |
| | Potassium hydroxide | Appropriate amt. | Appropriate amt. | Appropriate amt. | Appropriate amt. | Appropriate amt. | Appropriate amt. | Appropriate amt. | Appropriate amt. |
| | Purified Water | Balance | Balance | Balance | Balance | Balance | Balance | Balance | Balance |
| Total | | 100 | 100 | 100 | 100 | 100 | 100 | 100 | 100 |
| (B)/(C) | | 2.00 | 0.50 | 1.00 | 3.00 | 1.00 | 3.00 | 2.00 | 2.75 |
| (B)/(D) | | 0.67 | 0.33 | 1.00 | 1.50 | 0.50 | 0.75 | 0.33 | 1.47 |
| PH | | 3.7 | 3.7 | 3.7 | 3.7 | 3.7 | 3.7 | 3.7 | 3.7 |
| Evaluation | Foam quantity | 250 | 255 | 240 | 262 | 249 | 255 | 220 | 265 |
| | Cleansing power (%) | 79 | 76 | 75 | 74 | 78 | 75 | 74 | 80 |

TABLE 1-continued

| | | | | | | | | |
|---|---|---|---|---|---|---|---|---|
| Slippery feel during foaming Average score in parentheses | Exc. (4.7) | Exc. (4.4) | Exc. (4.2) | Exc. (4.5) | Exc. (4.8) | Exc. (4.2) | Exc. (4.2) | Exc. (4.6) |
| Slippery feel during rinsing Average score in parentheses | Exc. (4.7) | Good (3.6) | Good (3.7) | Good (3.9) | Exc. (4.8) | Good (3.9) | Exc. (4.3) | Good (3.6) |
| Slippery feel after drying Average score in parentheses | Exc. (4.5) | Exc. (4.1) | Good (3.9) | Exc. (4.0) | Exc. (4.2) | Good (3.9) | Exc. (4.2) | Good (3.8) |
| Softness after drying Average score in parentheses | Exc. (4.5) | Exc. (4.1) | Exc. (4.0) | Exc. (4.2) | Exc. (4.1) | Exc. (4.1) | Exc. (4.3) | Good (3.9) |
| Manageability after drying Average score in parentheses | Exc. (4.3) | Exc. (4.0) | Good (3.8) | Exc. (4.0) | Exc. (4.0) | Good (3.9) | Exc. (4.1) | Good (3.7) |

| | Component (weight %) | Example |||||||
|---|---|---|---|---|---|---|---|---|
| | | 9 | 10 | 11 | 12 | 13 | 14 | 15 |
| (A) | Ammonium lauryl ether (1) sulfate*¹ | 13.5 | — | 12 | 12 | 12 | 12 | 12 |
| | Sodium lauryl ether (2) sulfate*² | — | 12 | — | — | — | — | — |
| (B) | Polyoxy-propylene (3) octyl ether | 0.25 | 1 | — | 1 | 1 | 1 | 1 |
| | Polyoxy-propylene (2) octyl ether | — | — | 1 | — | — | — | — |
| (B') | Polyoxy-propylene (5) octyl ether | — | — | — | — | — | — | — |
| | Polyoxy-ethylene (3) octyl ether | — | — | — | — | — | — | — |
| (C) | Isodecyl glyceryl ether | 0.25 | 0.5 | 0.5 | — | 0.5 | 0.5 | 0.5 |
| | 2-Ethylhexyl glyceryl ether | — | — | — | 0.5 | — | — | — |
| (C') | Coconut oil fatty acid monoethanol-amide | — | — | — | — | — | — | — |
| (D) | Laurylhydroxy-sulfobetaine | 1 | 1.5 | 1.5 | 1.5 | 1 | 1.5 | 1.5 |
| (D') | Amidopropyl betaine laurate | — | — | — | — | 0.5 | — | — |
| Others | Malic acid | 0.75 | 0.75 | 0.75 | 0.75 | 0.75 | 0.75 | 0.75 |
| | Ethylene glycol distearyl ether | 2 | 2 | 2 | 2 | 2 | 2 | 2 |
| | Cationized Guar gum*³ | 0.5 | 0.5 | 0.5 | 0.5 | 0.5 | 0.5 | 0.5 |
| | Dimethylpoly-siloxane emulsion*⁴ | 1 | 1 | 1 | 1 | 1 | 1 | 1 |

TABLE 1-continued

|  |  |  |  |  |  |  |  |  |
|---|---|---|---|---|---|---|---|---|
|  | Benzyl alcohol | 0.3 | 0.3 | 0.3 | 0.3 | 0.3 | 0.3 | 0.3 |
|  | Polypropylene (7) glycol | 1 | 1 | 1 | 1 | 1 | 1 | 1 |
| Others | Sodium chloride | 0.3 | 0.3 | 0.3 | 0.3 | 0.3 | 0.3 | 0.3 |
|  | Potassium hydroxide | Appropriate amt. | Appropriate amt. | Appropriate amt. | Appropriate amt. | Appropriate amt. | Appropriate amt. | Appropriate amt. |
|  | Purified Water | Balance | Balance | Balance | Balance | Balance | Balance | Balance |
| Total |  | 100 | 100 | 100 | 100 | 100 | 100 | 100 |
| (B)/(C) |  | 1.00 | 2.00 | 2.00 | 2.00 | 2.00 | 2.00 | 2.00 |
| (B)/(D) |  | 0.25 | 0.67 | 0.67 | 0.67 | 1.00 | 0.67 | 0.67 |
| PH |  | 3.7 | 3.7 | 3.7 | 3.7 | 3.7 | 3 | 5 |
| Evaluation | Foam quantity | 205 | 220 | 255 | 240 | 210 | 245 | 252 |
|  | Cleansing power (%) | 73 | 74 | 82 | 76 | 70 | 78 | 78 |
|  | Slippery feel during foaming Average score in parentheses | Good (3.7) | Exc. (4.3) | Exc. (4.3) | Exc. (4.1) | Good (3.5) | Exc. (4.7) | Exc. (4.9) |
|  | Slippery feel during rinsing Average score in parentheses | Exc. (4.0) | Exc. (4.9) | Good (3.9) | Good (3.7) | Exc. (4.9) | Exc. (4.9) | Exc. (4.7) |
|  | Slippery feel after drying Average score in parentheses | Exc. (4.0) | Exc. (4.6) | Exc. (4.1) | Exc. (4.0) | Exc. (4.5) | Exc. (4.3) | Good (3.3) |
|  | Softness after drying Average score in parentheses | Exc. (4.0) | Exc. (4.7) | Good (3.9) | Good (3.7) | Exc. (4.6) | Exc. (4.0) | Exc. (4.0) |
|  | Manageability after drying Average score in parentheses | Exc. (4.0) | Exc. (4.1) | Good (3.9) | Good (3.8) | Exc. (4.5) | Exc. (4.0) | Good (3.1) |

TABLE 2

| Component (weight %) |  | Comparative Example |  |  |  |  |  |  |  |
|---|---|---|---|---|---|---|---|---|---|
|  |  | 1 | 2 | 3 | 4 | 5 | 6 | 7 | 8 |
| (A) | Ammonium lauryl ether (1) sulfate*[1] | 12 | 12 | 12 | 12 | 12 | 12 | 12 | 12 |
|  | Sodium lauryl ether (2) sulfate*[2] | — | — | — | — | — | — | — | — |
| (B) | Polyoxypropylene (3) octyl ether | 1 | 1.5 | — | — | 1 | 2 | 2.5 | — |
|  | Polyoxypropylene (2) octyl ether | — | — | — | — | — | — | — | — |
| (B') | Polyoxypropylene (5) octyl ether | — | — | — | — | — | — | — | 1 |
|  | Polyoxyethylene (3) octyl ether | — | — | — | — | — | — | — | — |

TABLE 2-continued

| | | | | | | | | | |
|---|---|---|---|---|---|---|---|---|---|
| (C) | Isodecyl glyceryl ether | — | — | 0.5 | 1.5 | 0.5 | 1 | 0.25 | 0.5 |
| | 2-Ethylhexyl glyceryl ether | — | — | — | — | — | — | — | — |
| (C') | Coconut oil fatty acid monoethanolamide | — | — | — | — | — | — | — | — |
| (D) | Laurylhydroxysulfobetaine | 1.5 | 1.5 | 1.5 | 1.5 | — | — | 0.25 | 1.5 |
| (D') | Amidopropyl betaine laurate | — | — | — | — | — | — | — | — |
| Others | Malic acid | 0.75 | 0.75 | 0.75 | 0.75 | 0.75 | 0.75 | 0.75 | 0.75 |
| | Ethylene glycol distearyl ether | 2 | 2 | 2 | 2 | 2 | 2 | 2 | 2 |
| | Cationized Guar gum*3 | 0.5 | 0.5 | 0.5 | 0.5 | 0.5 | 0.5 | 0.5 | 0.5 |
| | Dimethylpolysiloxane emulsion*4 | 1 | 1 | 1 | 1 | 1 | 1 | 1 | 1 |
| | Benzyl alcohol | 0.3 | 0.3 | 0.3 | 0.3 | 0.3 | 0.3 | 0.3 | 0.3 |
| | Polypropylene (7) glycol | 1 | 1 | 1 | 1 | 1 | 1 | 1 | 1 |
| | Sodium chloride | 0.3 | 0.3 | 0.3 | 0.3 | 0.3 | 0.3 | 0.3 | 0.3 |
| | Potassium hydroxide | Appropriate amt. | Appropriate amt. | Appropriate amt. | Appropriate amt. | Appropriate amt. | Appropriate amt. | Appropriate amt. | Appropriate amt. |
| | Purified Water | Balance | Balance | Balance | Balance | Balance | Balance | Balance | Balance |
| Total | | 100 | 100 | 100 | 100 | 100 | 100 | 100 | 100 |
| (B)/(C) | | | | | | | | | |
| (B)/(D) | | | | | | | | | |
| PH | | 3.7 | 3.7 | 3.7 | 3.7 | 3.7 | 3.7 | 3.7 | 3.7 |
| Evaluation | Foam quantity | 180 | 185 | 160 | 200 | 165 | 205 | 165 | 150 |
| | Cleansing power (%) | 65 | 68 | 60 | 65 | 60 | 66 | 58 | 55 |
| | Slippery feel during foaming Average score in parentheses | Fair (2.8) | Poor (2.4) | Fair (2.8) | Good (3.2) | Fair (3.0) | Fair (3.1) | Poor (2.4) | Fair (3.1) |
| | Slippery feel during rinsing Average score in parentheses | Fair (3.1) | Good (3.2) | Fair (2.5) | Poor (1.6) | Fair (2.5) | Poor (2.1) | Good (3.2) | Fair (2.8) |
| | Slippery feel after drying Average score in parentheses | Good (3.2) | Good (3.2) | Fair (2.5) | Poor (1.8) | Poor (2.0) | Poor (1.8) | Fair (2.6) | Fair (2.6) |
| | Softness after drying Average score in parentheses | Good (3.2) | Good (3.2) | Poor (1.5) | Poor (1.5) | Poor (1.8) | Poor (1.5) | Fair (2.5) | Poor (2.2) |
| | Manageability after drying Average score in parentheses | Good (3.2) | Good (3.2) | Fair (2.8) | Poor (2.4) | Poor (2.0) | Poor (1.8) | Fair (2.6) | Fair (3.0) |

TABLE 2-continued

| | Component (weight %) | Comparative Example | | | | | | | |
|---|---|---|---|---|---|---|---|---|---|
| | | 9 | 10 | 11 | 12 | 13 | 14 | 15 | 16 |
| (A) | Ammonium lauryl ether (1) sulfate*¹ | 12 | 12 | 12 | 12 | 12 | 12 | 12 | 12 |
| | Sodium lauryl ether (2) sulfate*² | — | — | — | — | — | — | — | — |
| (B) | Polyoxypropylene (3) octyl ether | — | 1 | 1 | — | 1 | 1 | 1 | 1 |
| | Polyoxypropylene (2) octyl ether | — | — | — | — | — | — | — | — |
| (B') | Polyoxypropylene (5) octyl ether | — | — | — | — | — | — | — | — |
| | Polyoxyethylene (3) octyl ether | 1 | — | — | — | — | — | — | — |
| (C) | Isodecyl glyceryl ether | 0.5 | — | 0.5 | — | 0.5 | 0.5 | 0.2 | 4 |
| | 2-Ethylhexyl glyceryl ether | — | — | — | — | — | — | — | — |
| (C') | Coconut oil fatty acid monoethanolamide | — | 0.5 | — | — | — | — | — | — |
| (D) | Laurylhydroxysulfobetaine | 1.5 | 1.5 | — | 1.5 | 0.33 | 10 | 0.33 | 10 |
| (D') | Amidopropyl betaine laurate | — | — | 1.5 | — | — | — | — | — |
| Others | Malic acid | 0.75 | 0.75 | 0.75 | 0.75 | 0.75 | 0.75 | 0.75 | 0.75 |
| | Ethylene glycol distearyl ether | 2 | 2 | 2 | 2 | 2 | 2 | 2 | 2 |
| | Cationized Guar gum*³ | 0.5 | 0.5 | 0.5 | 0.5 | 0.5 | 0.5 | 0.5 | 0.5 |
| | Dimethylpolysiloxane emulsion*⁴ | 1 | 1 | 1 | 1 | 1 | 1 | 1 | 1 |
| | Benzyl alcohol | 0.3 | 0.3 | 0.3 | 0.3 | 0.3 | 0.3 | 0.3 | 0.3 |
| | Polypropylene (7) glycol | 1 | 1 | 1 | 1 | 1 | 1 | 1 | 1 |
| | Sodium chloride | 0.3 | 0.3 | 0.3 | 0.3 | 0.3 | 0.3 | 0.3 | 0.3 |
| | Potassium hydroxide | Appropriate amt. | Appropriate amt. | Appropriate amt. | Appropriate amt. | Appropriate amt. | Appropriate amt. | Appropriate amt. | Appropriate amt. |
| | Purified Water | Balance | Balance | Balance | Balance | Balance | Balance | Balance | Balance |
| Total | | 100 | 100 | 100 | 100 | 100 | 100 | 100 | 100 |
| (B)/(C) | | | | | | 2 | 2 | 5 | 0.25 |
| (B)/(D) | | | | | | 3.03 | 0.10 | 3.03 | 0.10 |
| PH | | 3.7 | 3.7 | 3.7 | 3.7 | 3.7 | 3.7 | 3.7 | 3.7 |
| Evaluation | Foam quantity | 140 | 130 | 110 | 80 | 155 | 130 | 160 | 115 |
| | Cleansing power (%) | 50 | 45 | 40 | 38 | 64 | 70 | 73 | 65 |
| | Slippery feel during foaming Average score in parentheses | Fair (2.7) | Poor (1.8) | Poor (2.3) | Poor (1.2) | Fair (2.7) | Poor (2.4) | Poor (2.0) | Poor (1.5) |

TABLE 2-continued

|  | | | | | | | | |
|---|---|---|---|---|---|---|---|---|
| Slippery feel during rinsing Average score in parentheses | Poor (2.4) | Good (3.1) | Good (3.3) | Fair (2.4) | Poor (1.6) | Poor (1.4) | Poor (1-5) | Poor (1-2) |
| Slippery feel after drying Average score in parentheses | Fair (2.2) | Fair (2.8) | Poor (2.4) | Poor (1.5) | Fair (2.5) | Poor (2.2) | Poor (1-6) | Poor (1-3) |
| Softness after drying Average score in parentheses | Poor (1.7) | Poor (2.4) | Fair (2.8) | Poor (1.6) | Poor (1.9) | Poor (2.1) | Poor (1.8) | Poor (1.2) |
| Manageability after drying Average score in parentheses | Poor (2.2) | Poor (2.4) | Fair (2.6) | Fair (2.6) | Poor (1.8) | Poor (2.1) | Poor (1.6) | Poor (1.2) |

*¹'Emal 125A' by Kao Corporation, alkyl chain length C12:14 = 75:25. Original material effective content 25%, effective content concentration as given in this table.
*²'Emal 227' by Kao Corporation, alkyl chain length C12:14 = 75:25. Original material effective content 25%, effective content concentration as given in this table.
*³'Jaguar C-13S' by Rhodia
*⁴'Silicone CF2460' by Dow Corning Toray Silicone Co., Ltd. Original material effective content 75%, average particle size 30 μm. Effective content concentration as given in this table.
*⁵With respect to the Comparative Examples, the contents of components (B), (C), and (D) or components (B') (C'), (D') were used.
*¹'Emal 125A' by Kao Corporation, alkyl chain length C12:14 = 75:25. Original material effective content 25%, effective content concentration as given in Tables 1 and 2.
*²'Emal 227' by Kao Corporation, alkyl chain length C12:14 = 75:25. Original material effective content 25%, effective content concentration as given in Tables 1 and 2.
*³'Jaguar C-13S' by Rhodia
*⁴'Silicone CF2460' by Dow Corning Toray Silicone Co., Ltd. Original material effective content 75%, average particle size 30 μm. Effective content concentration as given in Tables 1 and 2.

From Tables 1 and 2, it can be seen that the compositions of the Examples had excellent lather and cleansing power under conditions of sebum soiling, excellent smoothness during foaming and during rinsing, and excellent hair smoothness, softness, and manageability after drying.

Formulation examples using the aqueous hair cleansing agent of the present invention are shown below.

Example 16

Shampoo

|  | (weight %) |
|---|---|
| Ammonium polyoxyethylene (1) lauryl ether sulfate | 12.0 |
| Polyoxypropylene (3) octyl ether | 0.65 |
| Monoisodecyl glyceryl ether | 0.35 |
| Laurylhydroxysulfobetaine | 1.70 |
| Malic acid | 0.75 |
| Myristyl alcohol | 0.40 |
| Cationized guar gum ('Jaguar C-17', Rhodia) | 0.28 |
| Cationized cellulose ('Poiz C-80M', Kao Corporation) | 0.25 |
| Diallyldimethylammonium chloride/acrylamide copolymer ('Merquat 550', OndeoNalco, effective content 8.5 weight %) | 1.8 |
| Polydimethylsiloxane ('Silicone CF2460', Dow Corning Toray Silicone Co., Ltd., effective content 75%, amount formulated was effective content concentration) | 1.0 |
| Ethylene glycol distearyl ether | 2.0 |
| Polypropylene glycol (mass average molecular weight 400) | 1.5 |

-continued

|  | (weight %) |
|---|---|
| Benzyl alcohol | 0.3 |
| Ethanol | 3.0 |
| Camellia oil | 0.01 |
| Panthenol | 0.05 |
| Royal jelly | 0.01 |
| Purified honey | 0.01 |
| Shea butter | 0.01 |
| Silk extract | 0.05 |
| Lanolin acid | 0.01 |
| Stearoxydimethylamine | 0.01 |
| Glycylglycine | 0.05 |
| Rose hip extract | 0.01 |
| Coconut extract | 0.01 |
| *Alpinia speciosa* leaf extract | 0.01 |
| Ginseng extract | 0.01 |
| Lotus flower extract | 0.01 |
| Licorice extract | 0.01 |
| Paramethylsulfonic acid | 0.35 |
| Sodium chloride | 0.2 |
| Fragrance | appropriate amount |
| pH adjusting agent (caustic potash) | amount to make pH 3.9 |
| Ion exchanged water | Balance |

Example 17

Shampoo

|  | (weight %) |
|---|---|
| Sodium polyoxyethylene (2) lauryl ether sulfate | 11.0 |
| Polyoxypropylene (3) octyl ether | 1.0 |
| Mono-2-ethylhexyl glyceryl ether | 1.0 |
| Laurylhydroxysulfobetaine | 2.0 |
| Polyoxyethylene (6) stearyl ether | 2.0 |
| Lauric acid | 0.8 |
| Dipotassium glycyrrhizinate | 0.1 |
| Coconut oil fatty acid monoethanolamide | 1.0 |
| Lauramidopropyl betaine | 0.5 |
| Cationized locust bean gum ('Catinal CLB-100', Toho Chemical Industry Co., Ltd.) | 0.2 |
| Cationized fenugreek gum ('Catinal CLB-100', Toho Chemical Industry Co., Ltd.) | 0.2 |
| Polydimethylsiloxane ('Silicone CF2450', Dow Corning Toray Silicone Co., Ltd., effective content 60%, amount added was effective content concentration) | 1.5 |
| Aminopolyether-modified silicone ('Silicone SILSTYLE 104', Dow Corning Toray Silicone Co., Ltd.) | 0.2 |
| Ethylene glycol distearyl ether | 1.5 |
| Dipropylene glycol | 3.0 |
| Benzyloxyethanol | 0.5 |
| l-Menthol | 1.0 |
| Sodium chloride | 0.2 |
| Fragrance | appropriate amount |
| pH adjusting agent (caustic soda) | amount to make pH 3.5 |
| Ion exchanged water | Balance |

It can be seen that Examples 16 and 17 had excellent lather and cleansing power even under conditions of sebum soiling, excellent smoothness during foaming and during rinsing, and excellent hair smoothness, softness, and manageability after drying.

The invention claimed is:

1. An aqueous hair cleansing agent comprising components (A), (B), (C) and (D):

(A) from 1 to 30 weight % of a sulfate anionic surfactant represented by formula (1)

$$R^1O(CH_2CH_2O)_nSO_3M \quad (1)$$

wherein, in formula (1), $R^1$ represents an alkyl group or alkenyl group having 10 to 18 carbon atoms, M represents an alkali metal, an alkaline earth metal, ammonium, an alkanolamine, or a basic amino acid, and n represents a number from 0 to 5 as a mass average;

(B) from 0.1 to 10 weight % of a polyoxypropylene alkyl ether nonionic surfactant represented by formula (2), $$R^2O(CH_2CH(CH_3)O)_mH \quad (2)$$

wherein in formula (2), $R^2$ represents a straight chain or branched alkyl group or alkenyl group having 8 to 10 carbon atoms, and m represents a number from 0.5 to 4 as a mass average;

(C) from 0.1 to 5 weight % of a monoalkyl glyceryl ether or monoalkenyl glyceryl ether nonionic surfactant having an alkyl group or alkenyl group having 4 to 12 carbon atoms; and (D) from 0.1 to 10 weight % of an alkylhydroxysulfobetaine amphoteric surfactant represented by formula (3)

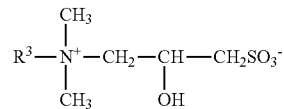

wherein, in formula (3), $R^3$ represents an alkyl group having 10 to 14 carbon atoms, and
wherein the mass ratio of components (B) and (D), (B)/(D), is 3/2 to 1/4.

2. The aqueous hair cleansing agent according to claim 1, wherein the mass ratio of components (B) and (C), (B)/(C), 3/1 to 1/2.

3. The aqueous hair cleansing agent according to claim 1, further comprising at least one (E) organic carboxylic acid or a salt thereof.

4. The aqueous hair cleansing agent according to claim 3, wherein component (E) comprises at least one member selected from the group consisting of glycolic acid, lactic acid, malonic acid, maleic acid and malic acid.

5. The aqueous hair cleansing agent according to claim 3, comprising component (E) at 0.1 to 5 weight % of the aqueous hair cleansing agent.

6. The aqueous hair cleansing agent according to claim 1, wherein the aqueous hair cleansing agent has a pH of 1 to 5 at 25° C. when diluted 20 times by weight with water.

7. The aqueous hair cleansing agent according to claim 1, wherein component (A) is a polyoxyethylene alkyl ether sulfate for which $R^1$ in formula (1) is an alkyl group having 12 to 14 carbon atoms, n represents a number from 1 to 2 as a mass average, and M is ammonium or sodium.

8. The aqueous hair cleansing agent according to claim 1, wherein component (B) is a polyoxypropylene octyl ether for which $R^2$ in formula (2) is an alkyl group having 8 carbon atoms and m is a number from 2 to 3 as a mass average.

9. The aqueous hair cleansing agent according to claim 1, wherein component (C) is a monoalkyl glyceryl ether nonionic surfactant having a 2-ethylhexyl group or an isodecyl group.

10. The aqueous hair cleansing agent according to claim 1, wherein component (D) is an alkylhydroxysulfobetaine amphoteric surfactant represented by formula (3)

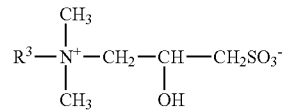

wherein, in formula (3), $R^3$ represents an alkyl group having 12 to 14 carbon atoms.

11. The aqueous hair cleansing agent according to claim 1, wherein the mass ratio of components (B) and (D), (B)/(D), is 3/2 to 1/3.

12. The aqueous hair cleansing agent according to claim 1, wherein the mass ratio of component (B) and (C), (B)/(C),is 2/1 to 1/1.

13. The aqueous hair cleansing agent according to claim 1, comprising from 9 to 15 weight % of component (A) by weight of the aqueous hair cleansing agent.

14. The aqueous hair cleansing agent according to claim 1, comprising from 0.3 to 2 weight % of component (B) by weight of the aqueous hair cleansing agent.

15. The aqueous hair cleansing agent according to claim 1, comprising from 0.2 to 3 weight % of component (C) by weight of the aqueous hair cleansing agent.

16. The aqueous hair cleansing agent according to claim 1, comprising from 0.5 to 3 weight % of component (D) by weight of the aqueous hair cleansing agent.

17. The aqueous hair cleansing agent according to claim 1, further comprising no greater than 0.5 weight % of an amphoteric surfactant other than component (D) by weight of the aqueous hair cleansing agent.

18. The aqueous hair cleansing agent according to claim 1, comprising an aliphatic amidopropyl betaine or an aliphatic alkanolamide as a surfactant other than component (D).

19. The aqueous hair cleansing agent according to claim 1, comprising from 0.01 to 10 weight % of a surfactant other than components (A), (B), (C), and (D).

20. The aqueous hair cleansing agent according to claim 1, wherein the aqueous hair cleansing agent has a pH of 2 to 4.5 at 25° C. when diluted 20 times by weight with water.

* * * * *